(12) United States Patent
Merz et al.

(10) Patent No.: US 8,864,311 B2
(45) Date of Patent: Oct. 21, 2014

(54) ILLUMINATION DEVICE AND OBSERVATION DEVICE

(75) Inventors: Franz Merz, Aalen (DE); Peter Reimer, Ellwangen (DE); Fritz Straehle, Heubach (DE)

(73) Assignee: Carl Zeiss Meditec AG, Jena (DE)

( * ) Notice: Subject to any disclaimer, the term of this patent is extended or adjusted under 35 U.S.C. 154(b) by 454 days.

(21) Appl. No.: 12/225,467

(22) PCT Filed: Mar. 23, 2007

(86) PCT No.: PCT/EP2007/002603
§ 371 (c)(1),
(2), (4) Date: Sep. 24, 2008

(87) PCT Pub. No.: WO2007/110207
PCT Pub. Date: Oct. 4, 2007

(65) Prior Publication Data
US 2009/0273757 A1 Nov. 5, 2009

(30) Foreign Application Priority Data
Mar. 24, 2006 (DE) .......................... 10 2006 013 761

(51) Int. Cl.
*A61B 3/00* (2006.01)
(52) U.S. Cl.
CPC ...................................... *A61B 3/00* (2013.01)
USPC .......................................................... 351/214
(58) Field of Classification Search
CPC ............... A61B 3/00; A61B 3/10; A61B 3/14
USPC .................... 351/200, 205, 206, 246
See application file for complete search history.

(56) References Cited

U.S. PATENT DOCUMENTS

| 3,926,500 | A | * | 12/1975 | Frosch et al. ................. 359/235 |
| 5,072,731 | A | | 12/1991 | Taratuta et al. |
| 5,867,251 | A | * | 2/1999 | Webb ............................ 351/221 |
| 6,003,993 | A | | 12/1999 | Webb |

(Continued)

FOREIGN PATENT DOCUMENTS

| DE | 2 021 784 A1 | 11/1970 |
| DE | 198 24 460 A1 | 12/1999 |

(Continued)

OTHER PUBLICATIONS

Harry Paul, Ed.: "Lexikon der Optik, Bd M bis Z" 2003, Springer Akademischer Verlag GmbH, Heidelberg, XP002439491.

*Primary Examiner* — James Greece
(74) *Attorney, Agent, or Firm* — Kriegsman & Kriegsman

(57) ABSTRACT

Among other things, an illumination device (10) is described for one, two or more observation beam paths, each with an observation device having an observation beam bundle, in particular for an operating microscope, having at least one light source (12) for producing at least one illumination beam bundle for illuminating an object to be observed (13), in particular, an eye to be observed, wherein the at least one illumination beam bundle runs coaxially to an observation beam bundle. It is provided according to the invention, in order to be able to suppress disruptive reflections, that illumination device (10) has an illumination optics (11) that is constructed according to the Köhler principle of illumination, and in which at least one reflection diaphragm (18) is provided in order to avoid light reflected from the surface of an objective element (19). In addition, a correspondingly improved observation device is described.

17 Claims, 1 Drawing Sheet

(56) References Cited

U.S. PATENT DOCUMENTS

| | | |
|---|---|---|
| 2004/0057108 A1 | 3/2004 | Namii |
| 2005/0128574 A1 | 6/2005 | Reimer et al. |
| 2007/0268575 A1 | 11/2007 | Yamazaki |
| 2009/0213329 A1 | 8/2009 | Kandel et al. |
| 2010/0309433 A1 | 12/2010 | Merz et al. |
| 2010/0321637 A1 | 12/2010 | Hoegele |

FOREIGN PATENT DOCUMENTS

| | | |
|---|---|---|
| DE | 10 2004 050 651 A1 | 3/2006 |
| JP | 1-255818 A | 10/1989 |
| JP | 2002-517774 A | 6/2002 |
| JP | 2005-118561 A | 5/2005 |
| WO | WO 02/26121 A1 | 4/2002 |

* cited by examiner

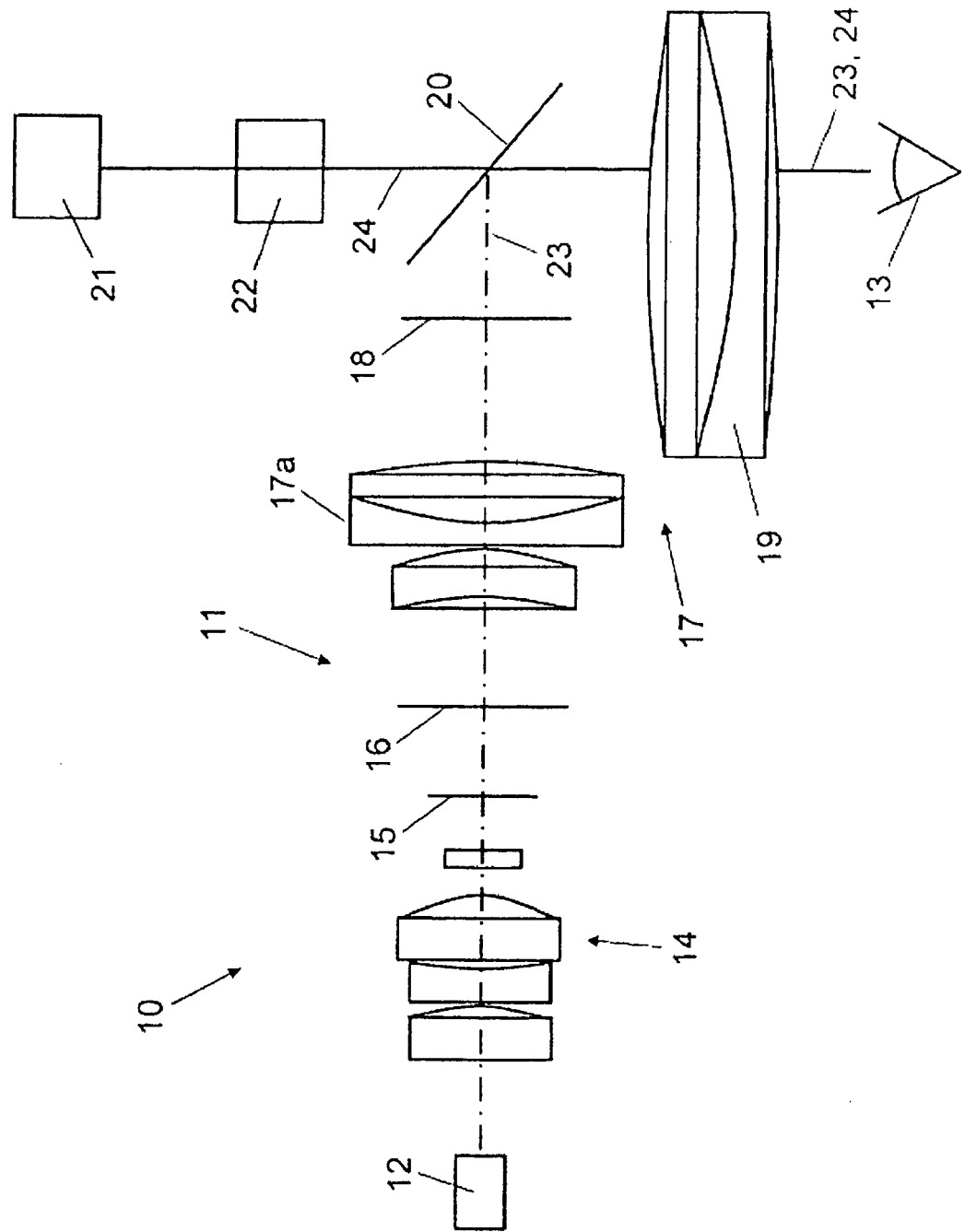

ILLUMINATION DEVICE AND OBSERVATION DEVICE

The present invention relates first to an illumination device For one or more observation beam paths, each with an observation device having an observation beam bundle, in particular for an operating microscope, having at least one light source for producing at least one illumination beam bundle for illuminating an object to be observed, in particular, an eye to be observed, wherein the at least one illumination beam bundle runs coaxially to an observation beam bundle. In addition, the invention relates to an observation device, in particular, an operating microscope, having one, two or more observation beam paths, each having an observation beam bundle and having an illumination device, having at least one light source for producing at least one illumination beam bundle for illuminating an object to be observed, in particular, an eye to be observed, wherein the at least one illumination beam bundle runs coaxially to an observation beam bundle.

For example, an observation device may involve an operating microscope. In particular, the observation device can be designed as an opthalmologic operating microscope, which is utilized, for example, for a special application in eye surgery, i.e., cataract surgery.

In the case of cataract surgery, a lens of the eye—which is clouded, for example, due to the cataract—is replaced by an artificial lens.

The lens of an eye is found inside a thin envelope, the so-called lens capsule. In order to remove the lens of the eye, access to the lens is created by a thin cut made in the lens capsule and the lens of the eye is first broken up into small pieces with a microsurgical instrument, and then these pieces are removed by means of an aspirating device.

This process takes place under microscopic observation—for example, under stereomicroscopic observation—employing a specially designed illumination device for such interventions. This illumination device presents both an illumination of the surrounding field, which is necessary for illuminating the entire operating field, as well as a red background illumination for the actual operating field limited to the pupil region of the lens of the eye, which is of decisive importance for the cataract operation. This red background illumination is based on the percentage of illuminating light, which, after passing through the transparent media of the eye finally strikes the retina, which appears red due to good blood perfusion, is reflected therefrom, and then can also be observed, of course, as an apparent red background illumination, by the surgeon by means of the operating microscope. This very characteristic red background illumination in cataract surgery is generally known in professional circles under the term "red reflex".

For an optimal recognition of details relevant to the cataract operation, a red background illumination that is as homogeneous as possible has been proven to be a necessary prerequisite for the surgeon. A first requirement of the illumination device is thus to assure a homogeneity of the red reflex that is as good as possible over the entire pupil of the patient.

For complete elimination of the pieces of the lens of the eye, which has been broken up into tiny pieces, and for good recognition of transparent membranes, for example, of the lens capsule, another requirement must be fulfilled, that is, a good phase contrasting of objects and, in fact, this contrast should also be provided as much as possible over the entire pupil of the patient.

For surgery on the eye, and here, in particular, in cataract operations, a homogeneous, bright "red reflex" is required along with a good phase contrasting of objects over the entire region of the patient's pupil.

The operating microscopes of the prior art fulfill these requirements for regions of the pupil of the eye that are of varying size. A compromise must always be found between the primary requirements of a good, homogeneous "red reflex" and a good phase contrasting of objects.

For the most part, illumination is provided at a small angle for observation. This has the consequence, however, that the "red reflex" does not appear uniformly bright over the patient's pupil. An illuminating angle between 2 and 4 degrees has previously proven favorable. At this angle, one obtains a good compromise between good contrasting and illumination of the patient's pupil. With this arrangement, however, the "red reflex" reacts sensitively to a rolling of the patient's eye during the operation. Additional problems may occur when the patient's pupil is small or in connection with the refraction of the patient's eye.

Tests with coaxial illumination in fact led to a good, homogeneous "red reflex", but to a poor phase contrasting of objects, and thus it has previously not proven suitable in practice. In this case, the illuminating optics were disposed such that an illuminating mirror (or prism) lay between the two beam paths of the stereomicroscope. Thus, this did not involve an exact 0° illumination, which would result from precisely the same direction as the observation.

One possibility for obtaining a homogeneous bright "red reflex" with simultaneous good contrast can be achieved by splitting the illumination beam into two partial beam bundles. In this way, each partial beam bundle is guided so that the object to be observed, for example, an eye, is illuminated from the same direction from which the observation is also made (0° illumination) for the left and the right observation beam paths of a (stereo) operating microscope. Such a solution is described, for example, in the older Application DE 10 2004 050 651 A1 of the Applicant.

A general problem with such "coaxial solutions" is that disruptive reflections may occur at optical interfaces, and here, in particular, at the principal objective element of the stereomicroscope, and these reflections negatively influence the observation of the surgical field, e.g., by bright spots in the visual field.

In the previously common illumination or observation systems, usually a coaxial illumination arrangement was not used, despite its advantages for the "red reflex", or however, in the past, other measures were taken, which have a number of disadvantages.

A stopping down of the reflections in the observation beam path, for example, leads to vignetting or image drop-outs. A greater decentering of the principal objective relative to the observation beam bundles requires, for example, clearly larger and thus more expensive optics. In addition, the correction of the prismatic color error that occurs with this solution is more time-consuming. A suppression of reflections could also be achieved, for example, by the use of polarized light. With such a solution approach, however, more than half of the light in the illumination is lost (through the polarizer). On the other hand, more than half of the light beamed back from the object is retained in the analyzer. In particular, the last-named point is a disadvantage for applications in the eye, since illumination must be made with correspondingly greater intensities.

Starting from the named prior art, the object of the present invention is to further develop an illumination device as well as an observation device of the type named initially, in order to further improve the desired optimizing. In particular, an illumination device as well as an observation device will be provided, by means of which the above-described disruptive reflections can be suppressed.

The problem is solved according to the invention by an illumination device for one, two or more observation beam paths, each with an observation device having an observation beam bundle, in particular for an operating microscope, having at least one light source for producing at least one illumination beam bundle for illuminating an object to be observed, in particular, an eye to be observed, wherein the at least one illumination beam bundle runs coaxially to an observation beam bundle, is hereby characterized in that the illumination device has an illumination optics that is constructed according to the Köhler principle of illumination, and in which at least one reflection diaphragm is provided in order to avoid light reflected from the surface of an objective element. The problem is also solved according to the invention by an observation device, in particular, an operating microscope, having one, two or more observation beam paths, each having an observation beam bundle and having an illumination device, having at least one light source for producing at least one illumination beam bundle for illuminating an object to be observed, in particular, an eye to be observed, wherein the at least one illumination beam bundle runs coaxially to an observation beam bundle, is hereby characterized in that the illumination device has an illumination optics that is constructed according to the Köhler principle of illumination, and in which at least one reflection diaphragm is provided in order to avoid light reflected from the surface of an objective element. The problem is also solved by a use of an illumination device, as described above in an operating microscope, in particular, in an ophthalmologic observation device, preferably in an operating microscope designed for cataract extraction. The problem is also solved by a use of an observation device as described above as an operating microscope, in particular, as an ophthalmologic observation device, preferably as an operating microscope designed for cataract extraction. Other An illumination device is provided for one, two or more observation beam paths, each with an observation device having an observation beam bundle, in particular for an operating microscope, having at least one light source for producing at least one illumination beam bundle for illuminating an object to be observed, in particular, an eye to be observed, wherein the at least one illumination beam bundle runs coaxially to an observation beam bundle. The illumination device has an illumination optics which is constructed according to the Köhler principle of illumination, and in which is provided at least one reflection diaphragm for masking reflected light, which is radiated from the surface of an objective element.

The term "masking" in the context of the present invention means that reflected light, which would otherwise be radiated away from the surface of an objective element, is avoided. The emergence of reflected light and its radiation away from the surface of an objective element can advantageously be completely prevented, or at least can be attenuated, by the reflection diaphragm.

According to the first aspect of the invention, thus, an illumination device is provided for one, two or more observation beam paths, each with an observation device having an observation beam bundle, in particular for an operating microscope, having at least one light source for producing at least one illumination beam bundle for illuminating an object to be observed, in particular, an eye to be observed, wherein the at least one illumination beam bundle runs coaxially to an observation beam bundle. The illumination device is hereby characterized according to the invention in that the illumination device has an illumination optics which is constructed according to the Köhler principle of illumination, and in which is provided at least one reflection diaphragm for avoiding light reflected from the surface of an objective element.

Reflections can be suppressed particularly in a coaxial illumination system for an observation device, in particular, for an operating microscope, by the illumination device according to the invention.

A true coaxial lighting is created with the present invention. "Coaxial" is therefore generally understood as an illumination near the axis. This includes both an illumination under precisely zero degrees as well as an oblique illumination at a very small angle near the axis. Therefore, those solutions with slight deviations from the coaxial illumination arrangement are also included by the present invention.

According to the invention, the illumination device is provided for an observation device, but the invention is not limited to specific types of observation devices. For example, but not exclusively, however, the observation device can involve an operating microscope. Several non-exclusive examples for possible application purposes in the field of operating microscopes are described in detail in connection with the observation device according to the invention.

In the simplest case, a single illumination beam bundle is provided, which produces a single illumination spot. Embodiments having two or more illumination beam bundles are also possible, however, whereby in each case, one illumination beam bundle produces one illumination spot. In the last-named case, the illumination beam bundles—when considered in their totality—each represent partial illumination beam bundles.

According to the invention, it is additionally provided that the illumination device has an illumination optics designed in a particular way. This illumination optics is first characterized in that it is designed according to the Köhler principle of illumination. The Köhler principle of illumination is already known in and of itself. It has now been found surprisingly that its use in the illumination device leads to the fact that the disruptive reflections can be suppressed.

First, the illumination device has a light source. In this case, the invention is not limited to specific designs for the light source. Several non-exclusive examples are explained in more detail in the further course of the description.

The illumination optics constructed according to the Köhler principle first has a collector. This collector can advantageously consist of one or more individual or combined lens element(s). In addition, an aperture diaphragm is provided. This can be designed, for example, as a fixed or a variable diaphragm. The light source is imaged by the collector as an intermediate image (aperture diaphragm).

In addition, a condenser also is a part of the Köhler illumination. The image of the light source advantageously lies in the focal point of the condenser for the illumination device according to the invention. Depending on the configuration each time, it can be provided that the condenser includes an objective element, which will be described in detail below. In such case, it can be provided that the intermediate image of the light source is imaged infinitely.

If the object to be observed involves an eye, the cornea of the eye can be illuminated telecentrically with the illumination device according to the invention. In addition, the eye again images the light source on the retina. This light is then reflected at the red retina and illuminates uniformly, intensively and in a contrast-rich manner the lens of the eye that is to be operated on.

Finally, an iris diaphragm—also called a lighting field diaphragm—which can be designed advantageously as a fixed or a variable diaphragm is also part of the Köhler illumination. The lighting field diaphragm is illuminated by the light source. This is advantageously imaged infinitely by the condenser part without objective element and then by the objective element onto the object to be observed, for example, onto the cornea of an eye under investigation. Such a construction advantageously makes possible a clearly separate and defined imaging of the lighting field diaphragm and the light source.

Advantageously, the illumination device can have at least one objective element. The objective element can also be designed as an objective element of an observation device, in particular, as its principal objective. However, this is not absolutely necessary.

In another embodiment, means can be provided in order to superimpose an observation beam bundle and an illumination beam bundle each time. These means can be configured in the most diverse way and disposed in the most diverse places. Several non-exclusive examples will be explained below for this purpose.

For example, it may also be provided that the means for superimposing are disposed in such a way that a superimposition of the observation beam bundle and the illumination beam bundle is made above the objective element. The superimposition of the observation beam bundle and the illumination beam bundle can be made, for example, in the parallel beam path above the principal objective.

For example, it may also be provided that the means for superimposing are disposed in such a way that a superimposition of the observation beam bundle and the illumination beam bundle is made underneath the objective element. The possibility thus also exists of superimposing the illumination beam bundle and the observation beam bundle underneath the principal objective. It is advantageous in this case, if the illumination beam bundle is inclined, corresponding to the focal length of the principal objective.

As has been stated above, the invention is not limited to specific types of designs of "superimposition means". For example, the means for superimposing can have at least one optical element in the form of a prism and/or a beam splitter plate and/or a mirror, e.g., a partially transparent mirror and/or a perforated mirror. Of course, the means may also be configured in another way, so that the invention is not limited to the named examples.

In an advantageous embodiment, the illumination between the objective element and a magnification system, e.g., a pancratic system, in the observation beam path, is reflected into the observation beam path with the use of a splitter plate.

The illumination light is imaged in this way by the objective element, which may involve, for example, the principal objective of the observation device, but it is also reflected at its surfaces.

In order to avoid this, in the illumination optics according to the invention, at least one reflection diaphragm is provided for avoiding light reflected from the surface of an objective element. This diaphragm can be designed, for example, as a fixed or a variable diaphragm.

Parts of the reflected light that forms are imaged in the eye of an observer by the observation optics of the observation device and thus lead to disruptive bright spots in the image.

This reflected light is, of course, a part of the illumination light that is utilized and is thus related to this. If the reflected light is then masked with a reflection diaphragm at one place in the illumination optics, parts of the illumination light that is utilized are also stopped down. The calculated localization of this disruptive reflected light shows differences in relation to the useful illumination light, and in fact is dependent on the site within the illumination optics. Each time depending on the position of the reflection diaphragm, the illumination light is clearly or slightly attenuated.

The light source, or the intermediate image of the light source, respectively, on the one hand, is radiated out in a defined angular region. The light that exits the light source spreads out. The larger the beam aperture is, the larger is the beam cross section of the light bundle with increasing distance from the light source or from the image of the light source, respectively.

The disruptive reflected light, on the other hand, however, is dependent on the angle at which it strikes the objective element, for example, the principal objective. A limited angular region of the reflected light is detected by the observation optics of the observation device.

The further away one is found from the intermediate image of the light source in the illumination device, the further away the disruptive reflected light in the illumination beam cross section migrates from the illumination axis. This means that larger angles of the beam apertures produce the disruptive light. The closer the reflection diaphragm is brought to the intermediate image of the light source, then the more the actual non-disruptive aperture region is masked.

The optimal arrangement of the reflection diaphragm in the illumination beam path thus represents a particular challenge. Advantageously, it may be provided that the reflection diaphragm is disposed in front of the superimposing means in the illumination beam path. In another embodiment, it may be provided that the reflection diaphragm is disposed in front of the objective element in the illumination beam path.

The optimal site for a reflection diaphragm lies as far removed as possible from the intermediate image of the light source. This may be, for example, in front of the superimposing means, e.g., the splitter plate.

For example, it may be provided that at least different individual diaphragms as described above are designed as fixed diaphragms or also as variable diaphragms. For example, at least one diaphragm can be designed as a discrete diaphragm, as an LCD (Liquid Crystal Display) display, as a DMD (Digital Mirror Device), as an LCOS (Liquid Crystal On Silicon) or as an FLCOS (Ferroelectric Liquid Crystal ON Silicon). Other transmissive or reflective displays are also conceivable.

As stated above, the invention is not limited to a specific number of light sources or their design. For example, a single light source can be provided, which first produces a single illumination beam bundle. For example, it may also be provided that two or more light sources are provided and that an illumination beam bundle will be produced by means of each light source. Thus, independent light sources can be used, whereby each light source produces its own partial illumination beam bundle.

In another advantageous design, it can be provided that a single light source is provided and that means for splitting the illumination beam bundle of the light source into two or more partial illumination beam bundles are provided. Here, this may involve suitable beam splitters in the form of prisms, partially transparent mirrors and similar means.

The present invention is not limited to the use of specific light sources. Several non-exclusive, advantageous examples will be named below for this purpose. For example, the at least one light source can be designed as a lamp, in particular as a halogen lamp or a xenon lamp, as a laser, as a non-thermal radiator, as a light guide, in particular as an optical-fiber light-guide bundle, as at least one LED (light-emitting diode), as at least one OLED (organic light-emitting diode), or similar source. Of course, combinations of different light sources are also possible.

Advantageously, the light source is formed from an arrangement of one or more miniature light source(s) that can be switched on individually or by regions. The illumination device is designed such that the geometry of the light field that it produces can be varied in a simple manner. In this way, the miniature light sources will be controlled—in particular, electronically—from the outside, preferably by a control device. Another feature provides that the miniature light sources can be controlled at least in regions in order to be able to adjust variable illumination geometries. This is particularly of advantage when producing annular illumination beam bundles. The invention is thereby not limited to specific sizes and/or shapes of regions. In the simplest case, a single point can be controlled in this way. Particularly when the luminous source is formed from a matrix comprised of individual miniature light sources, one or more miniature light sources can be controlled individually or in groups, whereby in the last-named case, individual miniature light sources can be combined into one region. Also, in this respect, the invention is not limited to concrete embodiments.

Advantageously, the light source can be formed from an arrangement of one or more light diode(s) (LEDs), in particular, organic light diode(s) (OLEDs). Organic light diodes were originally developed as microdisplays. Unlike LCDs, which require a backlighting, OLEDs themselves illuminate as Lambert radiators (surface or flat emitters).

As structured or patterned lighting sources, OLEDs offer a good light efficiency and small structures without intermediate dark spaces. Depending on the desired illumination geometry, individual miniature light sources can be turned on and others can remain turned off. The filling factor is higher in OLEDs as opposed to LEDs, which means that a higher packing density can be provided. The use of a display of LEDs or OLEDs makes possible a programmable switching of different lighting modes that may also be automated, for example, without having to move mechanical components, such as, e.g., phase contrast rings, filters, reducers and similar components. Particularly suitable, for example, are white OLEDs, whose spectrum is determined by a mixture of organic molecules.

A number of advantages can be provided by the previously described illumination device according to the invention. On the one hand, there is no loss of light in the observation beam path. In addition, there is no vignetting or image drop-outs due to diaphragms in the observation beam path. Also, expensive objectives are not necessary.

The basic feature of the illumination device according to the invention is that the illumination optics are constructed according to the Köhler principle of illumination. Another feature consists of the fact that at least one suitable diaphragm is provided in the illumination beam path in the form of a reflection diaphragm.

According to another aspect of the invention, an observation device is provided, in particular, an operating microscope, having one, two or more observation beam paths, each with an observation beam bundle and with an illumination device, having at least one light source for producing at least one illumination beam bundle for illuminating an object to be observed, in particular, an eye to be observed, wherein the at least one illumination beam bundle runs coaxially to an observation beam bundle. The observation device is hereby characterized according to the invention in that the illumination device has an illumination optics which is constructed according to the Köhler principle of illumination, and in which is provided at least one reflection diaphragm for avoiding light reflected from the surface of an objective element.

Advantageously, the illumination device is formed in the way described above, according to the invention, so that reference is made to the corresponding passages.

The observation device may have, for example, a principal objective element which is identical to an objective element of the illumination device. In addition, means can be provided in order to superimpose an observation beam bundle and an illumination beam bundle each time. The means for superimposing can be disposed in such a way that a superimposition of observation beam bundle and illumination beam bundle is made above the principal objective element.

In another configuration, it may be provided that the observation device has a principal objective element which is identical to an objective element of the illumination device, that means are provided in order to superimpose an observation beam bundle and an illumination beam bundle and that the means for superimposing are disposed in such a way that a superimposing of observation beam bundle and illumination beam bundle is made under the principal objective element.

The radii of the principal objective determine the direction of the reflected light and thus the reflected light detected by the observation optics of the observation device. The smaller the radius is for the upper surface of the principal objective, the smaller the amount of reflected light that falls in the observation optics.

A decentering of the observation channels, e.g., the observation stereo channels, relative to the principal objective also influences the reflected light that is detected. The more that the observation channels, e.g., the stereo channels, are decentered relative to the axis of the principal objective, the smaller the amount of reflected light that is detected.

It is advantageously provided that two or more observation beam paths are provided and that the observation beam paths are decentered with respect to the principal objective element.

Advantageously, the observation device can be designed as a stereoscopic observation device, in particular as a stereomicroscope. The optical system of an operating microscope basically consists of several structural elements, such as the tube, the base body of the microscope, etc. Additionally, it is possible in many operating microscopes to connect different added modules, such as, for example, a co-observer tube for an assistant observer, a video camera for documentation, or similar units.

Several assemblies can also be combined inside the base body of the microscope, such as, for example, an illumination device, a magnification device, the principal objective, or similar components. The characteristic value for the principal objective is its focal length, which establishes the working distance from the operating microscope to the surgical field and also has an influence on the total magnification of the microscope.

Preferably, a magnification system can be provided in the at least one observation beam path. For example, this may involve a device for changing magnification, with which different magnifications can be adjusted. In many cases of application, a magnification change in steps is fully sufficient. However, it is also possible to use pancratic magnification systems as the magnification system, by means of which a step-free magnification (zoom system) is possible.

In this way, it may be advantageously provided that the device pupil of the observation device, which has already been described further above, is disposed in the magnification system.

In addition, a tube element and an ocular element can be provided in the at least one observation beam path. The task of an ocular element is generally the post-magnification of the intermediate image forming in the tube, as well as perhaps compensating for possible refractive errors of the user of such a microscope.

In addition, it is advantageously provided that the object plane of the object to be investigated is formed in the front focal point of the principal objective. It is achieved in this way that the object to be investigated is imaged infinitely by the principal objective.

Advantageously, the observation device can be designed as a stereoscopic observation device, in particular as a stereomicroscope. In this case, the observation device provides two parallelly running observation beam paths.

According to a preferred embodiment, the observation device may involve a stereomicroscope according to the telescopic principle, which essentially consists of three optical component parts, i.e., principal objective, (afocal) zoom system as well as a binocular telescope made up of tube and eyepiece.

The observation beam bundles run between the individual component parts of the observation device, preferably in parallel, so that the individual component parts can be exchanged and combined in modular manner.

In a preferred way, an illumination device according to the invention as described above can be used in an operating microscope, in particular, in an opthalmologic observation device, preferably in an operating microscope designed for cataract extraction. Likewise, an observation device according to the invention as described above can be used advantageously as an opthalmologic observation device, preferably as an operating microscope designed for cataract extraction.

The invention will now be explained in more detail based on an embodiment example with reference to the attached drawing. The single FIGURE here shows in schematic representation an illumination device according to the invention for an observation device.

The FIGURE shows an illumination device 10, which can be used in an observation device designed as an operating microscope, in particular, as a stereo microscope.

The illumination device 10 has an illumination optics 11 that is constructed according to the Köhler principle of illumination. First, a light source 12 is provided, for example, an optical fiber or a bundle of optical fibers. The fiber end of one or more optical fiber(s) is imaged in an intermediate image in an aperture diaphragm 16 by a collector 14, which consists of one or more lens elements, each comprised of one or more lens members.

This image of light source 12 lies in the focal point of a condenser 17. In the present example, condenser 17 consists of a number of condenser lens elements 17a. In addition, it includes the principal objective of the operating microscope, which simultaneously also involves an objective element 19 for illumination device 10. In this way, the intermediate image of light source 12 is imaged infinitely.

The object to be observed 13 will involve an eye in the present example. Due to the configuration described above, the cornea of the eye under investigation 13 is illuminated telecentrically, and eye 13 images light source 12 again on the retina. This light is reflected at the red retina and illuminates uniformly, intensively and in a contrast-rich manner, the lens of the eye of the patient that is to be operated on, for example.

Light source 12 of illumination device 10 simultaneously illuminates a lighting field diaphragm 15. The latter is imaged infinitely by condenser part 17a without principal objective 19 and then by principal objective 19 onto the cornea of eye 13.

This construction of illumination optics 11 makes possible a clearly separate and defined imaging of lighting field diaphragm 15 and light source 12.

The illumination is reflected into observation beam path 24 between principal objective 19 and a magnifying device 22 of the operating microscope, e.g., a pancratic system, by means 20 for superimposing beam bundles, for example, by a splitter plate. In the present example, an observation optics 21, which is not explained in further detail, is provided for the observation, and this optics may comprise, for example, a tube, ocular elements and the like.

For simplification, only observation axis 24 is shown from the observation beam path. Likewise, for simplification, only illumination axis 23 is shown from the illumination beam path.

The illumination light is imaged in this way by the principal objective 19, but it is also reflected at its surfaces. Parts of this reflected light are imaged into the eye of an observer by observation optics 21 and thus lead to disruptive bright spots in the image.

This reflected light is, of course, a part of the illumination light that is utilized and is thus related to it. If the reflected light is then masked with a reflection diaphragm 18 at one place in the illumination optics 11, parts of the illumination light that is utilized are also stopped down. The calculated localization of this disruptive reflected light shows differences in relation to the useful illumination light, and in fact is dependent on the site within the illumination optics. Each time depending on the position of reflection diaphragm 18, the illumination light is clearly or slightly attenuated.

The light source 12, or the intermediate image of light source 12, respectively, on the one hand, is radiated out in a defined angular region. The light that exits light source 12 spreads out. The larger the beam aperture is, the larger is the beam cross section of the light bundle with increasing distance from light source 12 or from the image of the light source, respectively.

The disruptive reflected light, on the other hand, however, is dependent on the angle at which it strikes principal objective 19. A limited angular region of the reflected light is detected by observation optics 21.

The further away one is found from the intermediate image of light source 12 in illumination device 10, the further away the disruptive reflected light in the illumination beam cross section migrates from illumination axis 23. This means that larger angles for the beam aperture produce the disruptive light. Also, the closer the reflection diaphragm 18 is brought to the intermediate image of light source 12, the more the actual non-disruptive aperture region will be masked.

The optimal site for a reflection diaphragm 18 lies as far removed as possible from the intermediate image of light source 12. This is in front of superimposing means 20, e.g., the splitter plate, for illumination device 10 according to the invention. A reflection diaphragm 18 on superimposing means 20 or in the observation beam path between magnifying device 22 and principal objective 19, respectively, would stop down observation beam bundles.

The radii of the principal objective 19 determine the direction of the reflected light and thus the reflected light detected by observation optics 21. The smaller the radius is for the upper surface of the principal objective, the less the amount of reflected light that falls in observation optics 21.

A decentering of the observation channels, e.g., the observation stereo channels, relative to principal objective 19 also influences the reflected light that is detected. The more the observation channels, e.g., the stereo channels, are decentered relative to the axis of the principal objective, the smaller the amount of reflected light that is detected.

LIST OF REFERENCE NUMBERS

10 Illumination device
11 Illumination optics
12 Light source
13 Object to be observed
14 Collector
15 Lighting field diaphragm
16 Aperture diaphragm
17 Condenser
17a Condenser lens elements
18 Reflection diaphragm
19 Objective element
20 Means for superimposing beam bundles
21 Observation optics
22 Magnification device
23 Illumination axis
24 Observation axis

The invention claimed is:

1. An illumination device for an observation device, said observation device having one, two or more observation beam paths having an observation beam bundle for observing an eye to be observed, in particular for a surgical microscope, having at least one light source for producing at least one illumination beam bundle which produces an illumination spot for illuminating an eye to be observed, wherein the illumination beam bundle runs coaxially to the observation beam bundle, is hereby characterized in that illumination device has illumination optics that is constructed according to the Köhler principle of illumination, in which at least one reflection diaphragm is provided in order to avoid light reflected from the surface of an objective element and an optical element in the form of a prism and/or a beam splitter plate and/or a partially transparent mirror and/or a perforated mirror is provided to superimpose the observation beam bundle and the illumination beam bundle, the reflection diaphragm being disposed in front of the optical element in the illumination beam path.

2. The illumination device according to claim 1, further characterized in that the illumination optics has a collector, which consists of one or more individual or combined lens element(s).

3. The illumination device according to claim 1, further characterized in that the illumination optics has a lighting field diaphragm, which is designed as a fixed or a variable diaphragm.

4. The illumination device according to claim 1, further characterized in that the illumination optics has an aperture diaphragm, which is designed as a fixed or a variable diaphragm.

5. The illumination device according to claim 1, further characterized in that it has an objective element.

6. The illumination device according to claim 5, further characterized in that the objective element is also designed as an objective element of an observation device, in particular as its principal objective.

7. The illumination device according to claim 5, further characterized in that the reflection diaphragm is disposed in front of the objective element in the illumination beam path.

8. The illumination device according to claim 1, further characterized in that diaphragm is designed as a discrete diaphragm, as an LCD display, as a DMD, as an LCOS or as an FLCOS.

9. The illumination device according to claim 1, further characterized in that two or more light sources are provided and that an illumination beam bundle will be produced by means of each light source.

10. The illumination device according to claim 1, further characterized in that a single light source is provided and that means for splitting the illumination beam bundle of the light source into two or more partial illumination beam bundles is provided.

11. The illumination device according to claim 1, further characterized in that the at least one light source is designed as a lamp, in particular as a halogen lamp or a xenon lamp, as a laser, as a non-thermal radiator, as a light guide, in particular as an optical-fiber light-guide bundle, as at least one LED, or at least one OLED.

12. An observation device, in particular, a surgical microscope, having one, two or more observation beam paths, each having an observation beam bundle for observing an eye to be observed and having an illumination device, having at least one light source for producing at least one illumination beam bundle which produces an illumination spot for illuminating an eye to be observed, wherein the illumination beam bundle runs coaxially to the observation beam bundle, is hereby characterized in that illumination device has illumination optics that is constructed according to the Köhler principle of illumination, in which at least one reflection diaphragm is provided in order to avoid light reflected from the surface of an objective element and an optical element in the form of a prism and/or a beam splitter plate and/or a partially transparent mirror and/or a perforated mirror is provided to superimpose the observation beam bundle and the illumination beam bundle, the reflection diaphragm being disposed in front of the optical element in the illumination beam path.

13. The observation device according to claim 12, further characterized in that the observation device has a principal objective element, which is identical to an objective element of illumination device, that means is provided in order to superimpose an observation beam bundle and an illumination beam bundle each time and that means for superimposing is disposed in such a way that a superimposition of the observation beam bundle and the illumination beam bundle is made above principal objective element.

14. The observation device according to claim 12, further characterized in that the observation device has a principal objective element, which is identical to an objective element of the illumination device, that means is provided in order to superimpose an observation beam bundle and an illumination beam bundle and that means for superimposing is disposed in such a way that a superimposition of the observation beam bundle and the illumination beam bundle is made below principal objective element.

15. The observation device according to claim 13, further characterized in that two or more observation beam paths are provided and that the observation beam paths are decentered with respect to the principal objective element.

16. A use of an illumination device according to claim 1 in an operating microscope, in particular, in an ophthalmologic observation device, preferably in an operating microscope designed for cataract extraction.

17. A use of an observation device according to claim 12 as an operating microscope, in particular, as an ophthalmologic observation device, preferably as an operating microscope designed for cataract extraction.

* * * * *